United States Patent [19]

Reyes

[11] Patent Number: 5,494,050
[45] Date of Patent: Feb. 27, 1996

[54] ARTHROSCOPY POUCH

[75] Inventor: Rogelio Reyes, El Paso, Tex.

[73] Assignee: Baxter International Inc., Deerfield, Ill.

[21] Appl. No.: 252,938

[22] Filed: Jun. 1, 1994

[51] Int. Cl.$^6$ .......................... A61B 19/00; A61B 19/08
[52] U.S. Cl. ............................ 128/849; 128/853
[58] Field of Search ................... 128/849–856

[56] References Cited

U.S. PATENT DOCUMENTS

| | | |
|---|---|---|
| 3,650,267 | 3/1972 | Anderson . |
| 3,856,005 | 12/1974 | Sislian . |
| 3,856,006 | 12/1974 | Krzewinski . |
| 3,881,474 | 5/1975 | Krzewinski . |
| 3,882,859 | 5/1975 | Ericson . |
| 3,923,052 | 12/1975 | Zoephel . |
| 3,956,048 | 5/1976 | Nordgren . |
| 4,089,331 | 5/1978 | Hartigan et al. . |
| 4,489,720 | 12/1984 | Morris ................................ 128/853 |
| 4,524,767 | 6/1985 | Glassman . |
| 4,559,937 | 12/1985 | Vinson . |
| 4,570,628 | 2/1986 | Neal . |
| 4,586,498 | 5/1986 | Morris . |
| 4,596,245 | 6/1986 | Morris . |
| 4,598,458 | 7/1986 | McAllester . |
| 4,616,642 | 10/1986 | Martin et al. . |
| 4,664,103 | 5/1987 | Martin et al. . |
| 4,869,271 | 9/1989 | Idris . |
| 4,873,997 | 10/1989 | Marshall . |
| 4,889,136 | 12/1989 | Hanssen . |
| 4,890,628 | 1/1990 | Jackson ................................ 128/853 |
| 4,974,604 | 12/1990 | Morris ................................ 128/853 |
| 5,002,069 | 3/1991 | Thompson ........................... 128/853 |
| 5,038,798 | 8/1991 | Dowdy et al. . |
| 5,042,507 | 8/1991 | Dowdy . |
| 5,107,859 | 4/1992 | Alcorn et al. . |
| 5,143,091 | 9/1992 | Patnode ............................... 128/849 |
| 5,161,544 | 11/1992 | Morris ................................ 128/853 |
| 5,209,243 | 5/1993 | Glassman ............................ 128/849 |
| 5,322,071 | 6/1994 | Ambrose ............................. 128/853 |

*Primary Examiner*—Michael A. Brown
*Attorney, Agent, or Firm*—Robert A. Stenzel; Kay H. P. Hannafan; Paul C. Flattery

[57] ABSTRACT

A surgical drape is described which includes a pouch having one embodiment a one-piece construction and formed with a single seam. An edge of the pouch may be extended to create a concave surface to control and contain fluids during a surgical procedure. Once formed or shaped into the pouch and the edge sealed, the sheet has a front portion, a back portion, an upper back edge in the back portion for placement relatively near the surgical site, and an upper front edge on the front portion, which in the final configuration, is located away from the upper back edge. The upper back edge and the upper front edge together define the opening in the pouch having a circumference. Additionally, the length of the upper front edge is preferably greater than the length of the upper back edge.

27 Claims, 4 Drawing Sheets

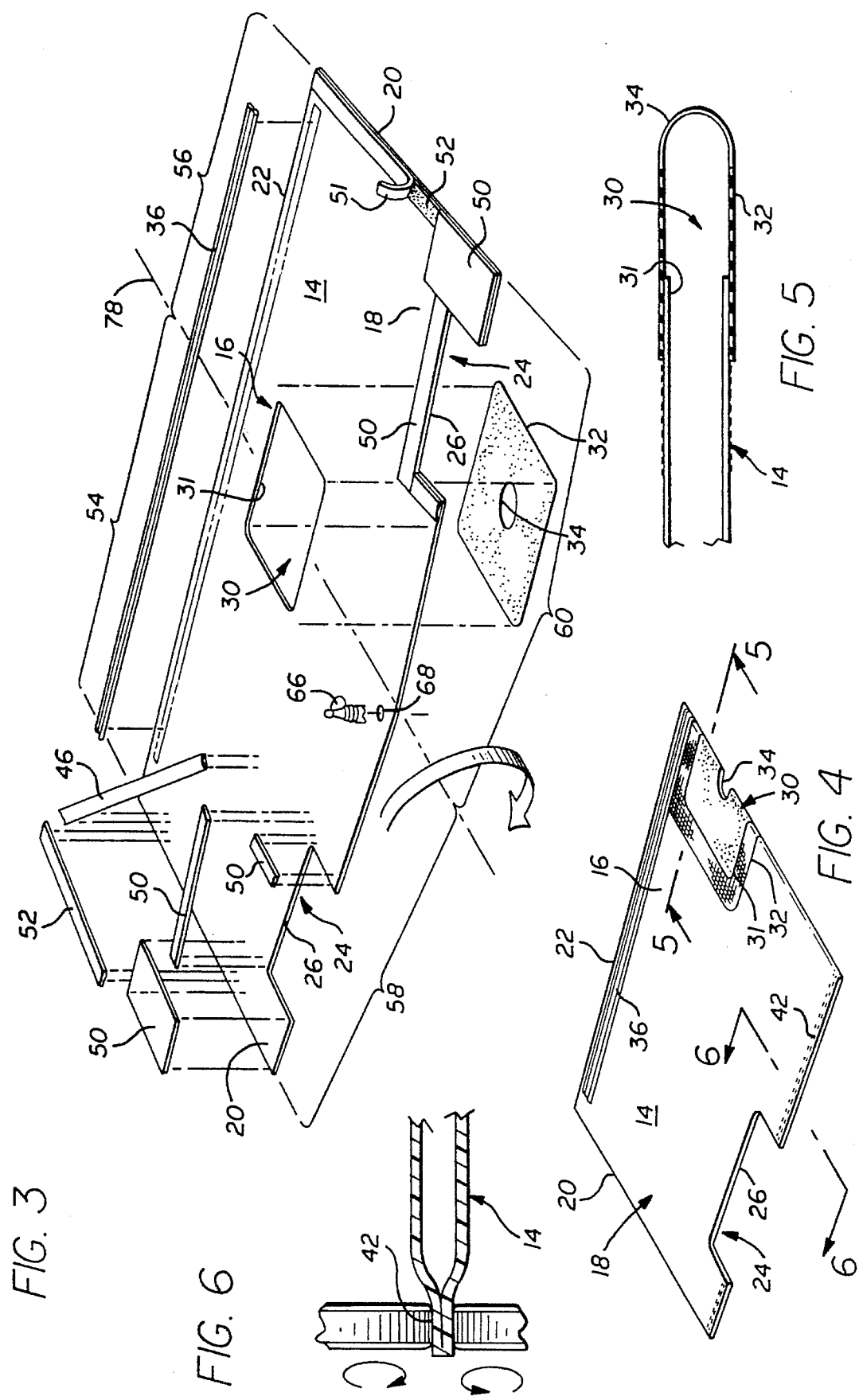

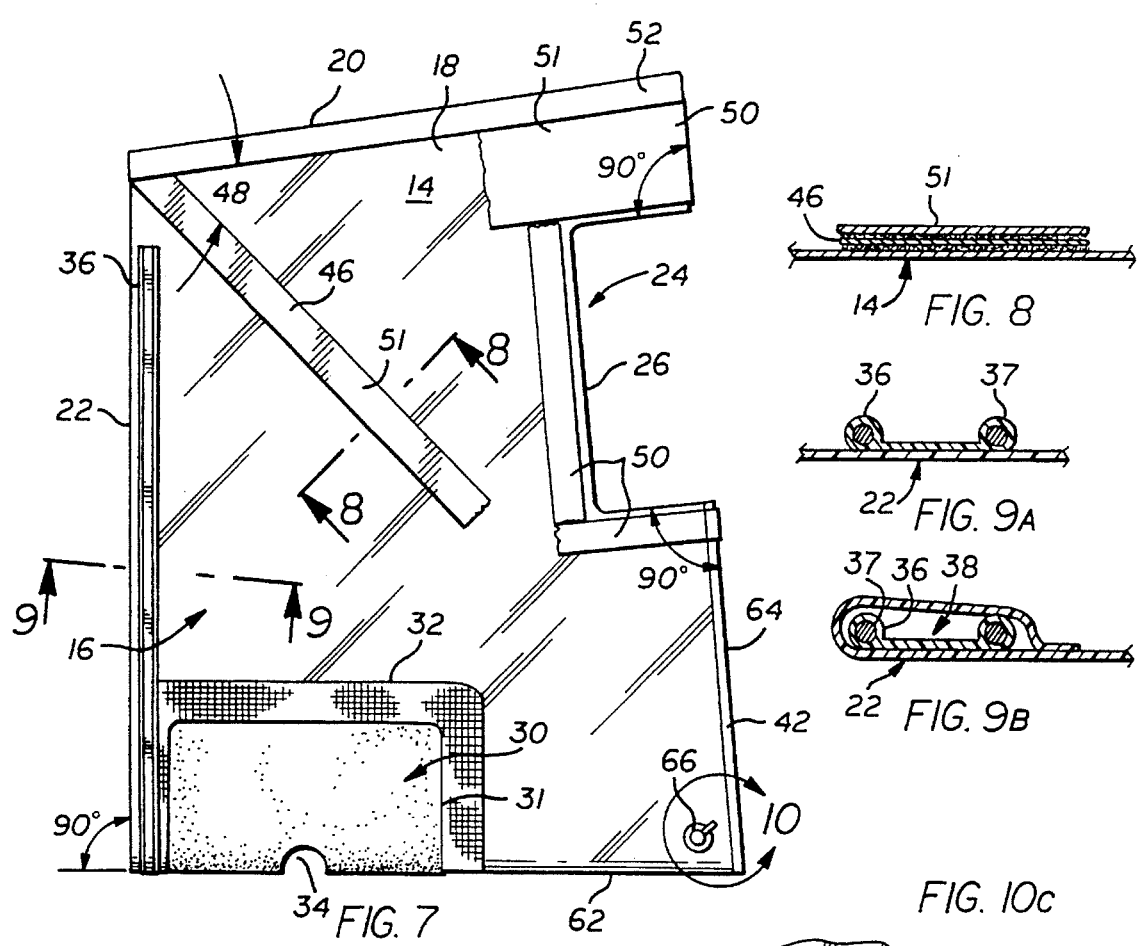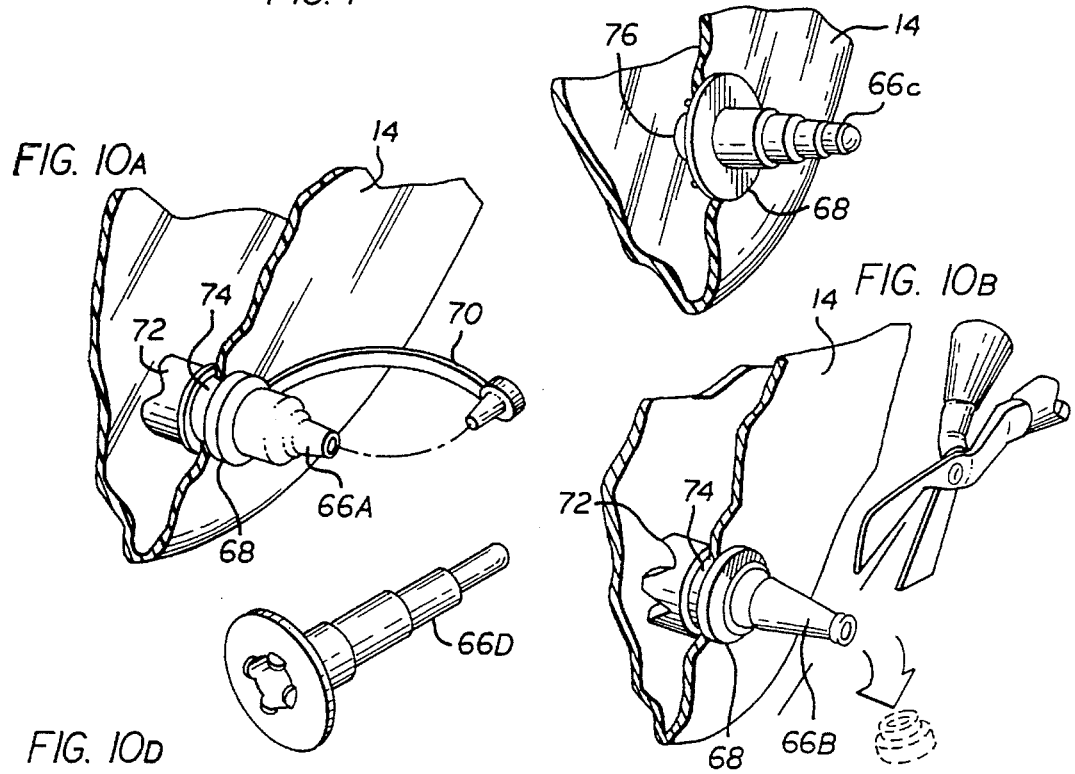

ARTHROSCOPY POUCH

BACKGROUND OF THE INVENTION

1. Field of the Invention

The present invention relates to fluid collection pouches or bags for use in surgical procedures to collect, channel and contain fluids from a surgical site during an operation, and more specifically to pouches such as arthroscopic fluid collection pouches and to pouch and drape assemblies. The invention also relates to methods of making such pouches and such pouch and drape assemblies.

2. Related Art

During many surgical procedures, it is frequently desirable to create a sterile field around a surgical site to reduce the possibility of infection of a patient. Typically, a sterile field is created by draping a sterile material over a patient in such a manner as to leave an opening only at the actual site of an incision. Such surgical drapes have been used for many years. Originally, the focus of draping was to protect the patient from infection. Recently, that focus has expanded to include protection of the surgical staff from infection. Examples of the types of infection that a staff member may be exposed to from fluids include the hepatitis B virus and the AIDS virus. Thus, another function of surgical drapes used today is to provide a barrier to the exposure of liquids or bacteria which may result in contamination of the patient or the staff performing the surgical procedure.

In some surgical procedures very large volumes of fluid may be present either from irrigation sources or from the patient's body fluids. It is desirable in most instances to control and contain such fluids. Some drapes have been used in the past which contain a pouch to collect fluids present during surgery. Collection of the fluids in the pouch also facilitates disposal of the fluids after the surgery.

Fluid collection pouches are commonly used in a number of surgical procedures. Cranial procedures, endourological operations, ophthalmic procedures and arthroscopic surgery use fluid collection pouches to collect, contain and facilitate disposal of fluids produced during the procedure. In arthroscopic surgery, patient blood, other body fluids, as well as irrigation fluid used to flush material from the joint, is collected in the fluid collection pouch.

Fluid collection during arthroscopic procedures is different in some respects from fluid collection during other surgical procedures. For example, using a collection pouch to collect and contain fluid during abdominal surgery has the fluid collection pouch placed adjacent one side of the surgical site and extending down the side of the patient. Arthroscopy procedures typically place a patient's leg through a collection pouch mounted to a drape with one sheet of the collection pouch in front of the surgical site on the limb and another sheet of the collection pouch in back of the surgical site. Therefore, the fluid collection pouch is supported in part by the limb itself, as well as by the surgical drape to which the fluid collection pouch is attached.

One disadvantage of the currently available disposable collection pouches is that they are formed of separate sheets sealed together, and may leak. Leaks may form at any number of seals in the pouch when the pouch is pulled outward or is opened before the procedure for collecting fluids. As many as five seals may be used in the construction of a single bag, each of which may present a risk of leakage in the pouch.

A relatively large number of seals used in assembling a fluid collection pouch uses significant labor and assembly time. Depending on the complexity of a collection pouch design, the location and the positioning of the seal lines may substantially add to handling time. This additional time and labor represents a significant increase in the cost of production for disposable fluid collection bags.

Another disadvantage of prior fluid collection pouches is that they are relatively complicated to manufacture in that they require the joining of multiple sheets to form a pouch that is conformable to the body of a patient to control fluids. For certain applications, the collection pouch pattern may be more complicated in order to control fluids released at a particular surgical site, such as the arm or leg of a patient. Substantial labor steps may be necessary for forming odd-shaped patterns, or for joining multiple sheets of material into a pattern for a pouch specifically constructed for controlling fluids during surgery, such as an arthroscopic procedure.

Another disadvantage of some fluid collection bags, particularly for use during surgical procedures on a patient's leg, is that the collection pouch may not extend forward and away from the patient far enough to adequately expose a surgical site, and it may not provide an opening large enough for capturing fluids. The opening in a conventional fluid pouch, for example, may be symmetrical and relatively simple to manufacture and pack. However, a symmetrical opening in a fluid pouch may not adequately control fluid at an irregularly-shaped area of a body, such as the leg of a patient.

Some conventional collection pouches having extended portions to control fluids during a surgical procedure formed of multiple sheets of flexible plastic that require multiple seals and multiple sealing steps. One disadvantage of these pouches is that they require separate sheets of plastic and a significant number of seals. The increased number of seals in a collection bag generally increases the risk of fluid leakage and the spread of infection, in addition to an added cost of assembly.

Therefore, there is a need for a fluid collection pouch and for a pouch and surgical drape assembly which minimizes the possibility of leaks developing during use, such as at seal points, and which is easier to assemble and use.

SUMMARY OF THE INVENTION

In view of the foregoing, it is an object of the present invention to provide a more reliable fluid collection pouch that can be economically formed from one sheet of flexible fluid impermeable material for channeling, collection and control of fluid during surgical procedures.

Another object of the invention is to provide a pouch that can be formed using a single seal joining edges of a sheet of flexible fluid impermeable material cut and folded to provide the pouch with an opening that extends forward and away from a patient.

It is also another object of the invention to provide a fluid collection pouch that has an exit port with a reliable seal to minimize the possibility of leaking around the port.

Another object of the invention is to provide a method of manufacturing an economical fluid collection pouch formed with a single seal that is resistant to tearing.

Further object of the invention is to provide a method of manufacturing a fluid collection pouch that is joined with a surgical drape where the pouch has a single seam positioned adjacent the drape and between spaced apart points where the pouch is joined to the drape so that the drape serves to reinforce the pouch.

These as well as other objects are achieved through the present invention which provides a fluid collection pouch, such as for a pouch and surgical drape assembly, which minimizes the possibility of leaks developing during use and which is easier to use and assemble. In one preferred form of the invention, a pouch is preferably formed with a single seal, preferably at a rear portion of the pouch, joining edges of the sheet to form the pouch. In one preferred embodiment, the pouch is formed from a single sheet of flexible, fluid impermeable material folded in such a way as to form the pouch once the single seal is formed.

In another preferred form of the invention, the pouch is formed from a sheet of flexible fluid impermeable material initially rectangular, and which has the edges of preferably a long side cut, from a center line parallel to the short sides, downward in a direction toward the opposite long side. The resulting cut long side will thereafter form an upper back edge spaced from an upper front edge, and the cutting of the long side gives a final pouch which has an effectively wider opening as defined by the upper back and front edges.

In a further preferred form of the invention, a single seam fluid collection pouch is attached to a surgical drape having an opening therethrough so the seam is in the back of the pouch positioned between the junction points between the pouch and the drape so that the drape reinforces the pouch material around the seam and isolates the seam from stress which may be created elsewhere in the pouch.

These and other aspects of the invention will become apparent from a consideration of the drawings, a brief description of which follows, along with a consideration of the preferred embodiments.

BRIEF DESCRIPTION OF THE DRAWINGS

FIG. 3 is a partially exploded and perspective view of a sheet of material and components used to form the pouch of the present invention showing cuts made in the sheet and adhesive tape and release paper, a fenestration and contour wire.

FIG. 4 is a perspective view of the pouch of FIG. 1 in a folded, flat configuration prior to application of adhesive and attachment to a conventional surgical drape.

FIG. 5 is a partial cross-sectional view of the front fenestration and the folded pouch taken along a line 5—5 in FIG. 4.

FIG. 6 is a partial cross-sectional view of the single seal joining a common edge of the flexible sheet of plastic material to itself, taken along the line 6—6 in FIG. 4, along with a schematic representation of sealing rollers for forming the seal.

FIG. 7 is a detailed top plan view of a complete pouch in accordance with the embodiment of FIGS. 1 and 4 in a folded configuration and showing release paper covering adhesive for use in attaching the pouch to a conventional drape.

FIG. 8 is a cross-sectional view of the pouch and double-faced adhesive tape with release paper taken along line 8—8 in FIG. 7 in accordance with one embodiment of the present invention.

FIG. 9A is a cross-sectional view of the contour wire support in FIG. 7 in accordance with one embodiment of the invention.

FIG. 9B is a cross-sectional view of the contour wire support in a preferred embodiment of the invention taken along line 9—9 in FIG. 7.

FIGS. 10A and 10B are partial cut-away perspectives of exit ports in accordance with the invention.

FIG. 10C is a partial cut-away perspective of a heat sealable exit port in accordance with one aspect of the preferred embodiment.

FIG. 10D is a perspective of an alternate exit port in accordance with the invention.

DETAILED DESCRIPTION OF THE PREFERRED EMBODIMENTS

Figure 1:
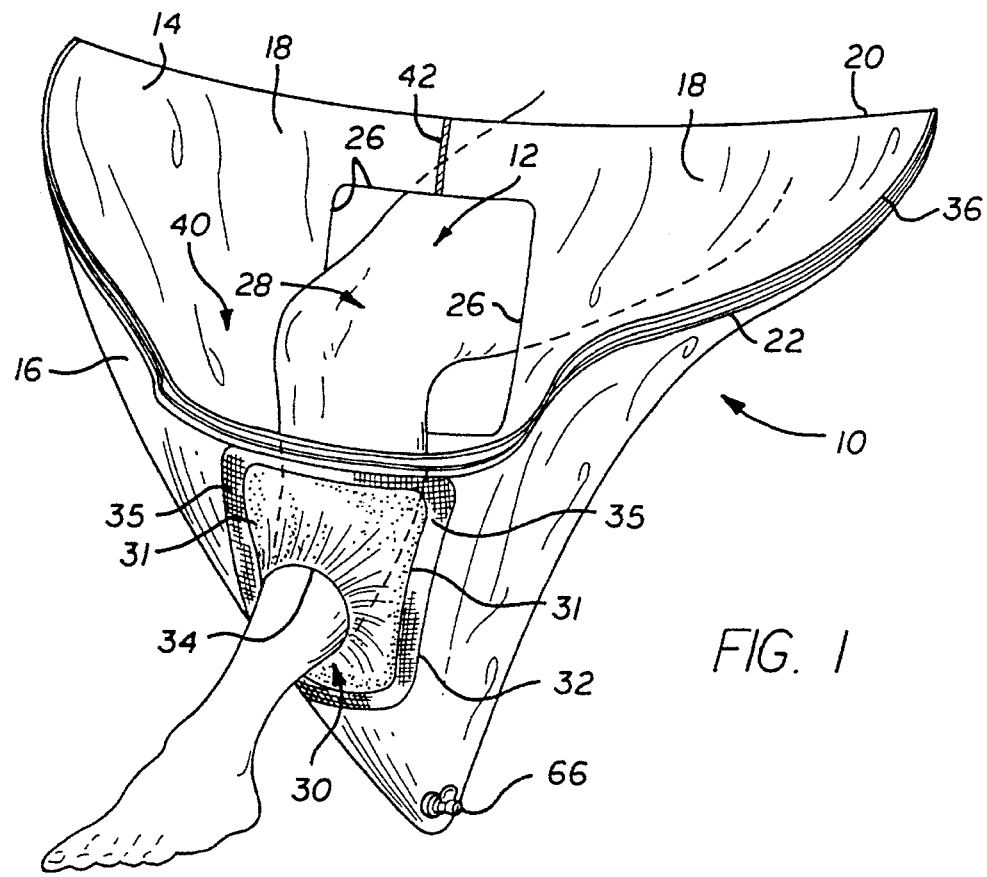
FIG. 1 is a perspective view of one embodiment of the invention when the pouch is in the open position, showing a patient's leg for environment but omitting the conventional accompanying surgical drape for clarity.

In accordance with the present invention, a fluid collection pouch is provided which minimizes the potential for leaking. In one preferred aspect of the present invention, a pouch 10 (FIG. 1) is provided for channeling, controlling and collecting fluids from a surgical site 12. The pouch 10 is preferably formed essentially from one sheet of flexible fluid impermeable material 14 for minimizing the number of seams or seals used in the pouch.

The sheet has a front portion 16, a back portion 18, an upper back edge 20 in the back portion for placement in close proximity to the surgical site 12, and an upper front edge 22 in the front portion located spaced apart from the upper back edge 20, when the pouch is properly positioned and opened. The reference to one sheet refers to the enclosure portion of the pouch, namely that portion typically attached to a draft and forming an opening for collecting fluid, and which also may accept attachment of other elements such as adhesive, elastomeric material, and the like.

In the application of an arthroscopy pouch, the pouch includes one or more openings for accepting the limb of the patient and for supporting the pouch on the patient's limb. Specifically, a back fenestration 24 is defined by walls 26 (FIG. 1–3) in the back portion 18 for passing over the patient's leg 28 to be positioned above the surgical site 12, and a front fenestration 30 is defined by walls 31 in the front portion 16 for passing over the patient's leg and which will be positioned below the surgical site 12, when the pouch 10 is fully opened to the configuration shown in FIG. 1. It should be noted that the pouch 10 is typically attached, joined or mounted to a conventional surgical drape 44 (FIG. 12) having an encircling sheet (described more fully below) for surrounding the leg 28, but the drape is omitted from FIG. 1 for clarity. In one embodiment of the invention, as illustrated in FIGS. 1 and.2, the front fenestration 30 of the pouch 10 is further defined by a sheet of an elastomeric material 32, with an opening or fenestration 34, attached by heat sealing or adhesive at 35 to the sheet 14 from which the pouch 10 is formed. The fenestration 34 of the elastomeric sheet 32 conforms to the contours of the body member which passes through the fenestration 34, such as a patient's leg 28, and has a size smaller than that of the front fenestration 30. In part, the body member 28 supports the fluid collection pouch 10 since the elastomeric material 32 rests directly on the body member, which in turn, supports the front portion 16 of the pouch 10.

In the preferred embodiment, the upper front edge 22 includes a malleable and formable contour wire or draw wire 36 for configuring and shaping the front portion 16 of the pouch 10, such as through manipulation of the contour wire, in the conventional manner. In the preferred embodiment, the contour wire 36 is positioned and retained in at least one channel 38 (FIG. 9B), which extends along at least a portion of the upper front edge 22. The contour wire 36 positioned at the upper edge 22 of the front portion 16 allows at least a portion of the upper front edge to be formed into a generally concave surface 40. The concave surface 40, along with the back portion 18, controls and contains fluids from the surgical site 12. The draw wire 36 within the channel 38 of the upper front edge 22 maintains the upper front edge in a relatively fixed position throughout a surgical procedure without repeated adjustment or manipulation by the operating room staff.

As shown in FIGS. 1, 4, 6, 7 and 11–13, the sheet of flexible plastic material 14 is preferably joined and sealed at a single seam 42. In the preferred embodiment, the seam 42 is located in the proximity of the center of the back portion 18 so as to be isolated from possible stresses that may arise by pulling on other parts of the pouch 10, such as at the front portion 16 when the pouch is first opened. The seam 42 may be formed in one embodiment by heat sealing the ends of sheet 14 between rollers as shown in FIGS. 4 and 6. The seam 42 may also be formed by a thermoimpulse pressure bar machine, such as to create a quarter-inch seam. Although the seam 42 is preferably formed by one seal line along the sheet 14, multiple seal lines may be used to form the seam. It is desirable to locate the seam 42 away from the edges of the pouch 10 where the pouch is attached to the surgical drape 44 (FIG. 12), e.g. where the front portion 16 and the rear portion 18 meet, and more significantly where the upper front edge 22 and upper back edge 20 meet, since this juncture is a location where tearing may occur. For example, when front edge 22 is pulled open and away from the patient to further expose the surgical site 12, seams which might be located at the juncture between the front portion 16 and the back portion 18, or seams located near the point where a staff member may grasp the plastic, are susceptible to tearing. Therefore, it is preferable not to have other seams located on the front portion 16, and preferably not elsewhere on the back portion 18 of the pouch, so that the risk of tearing is reduced.

Figure 12:
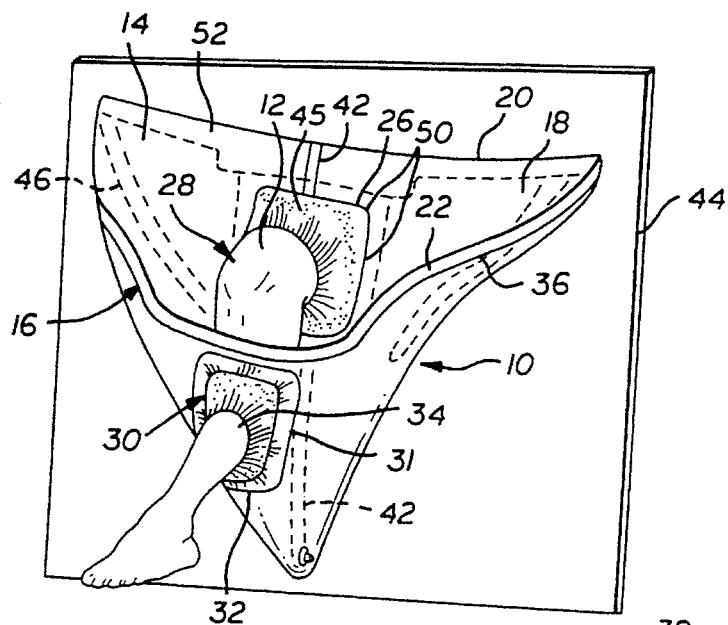
FIG. 12 is a front perspective of the pouch of one embodiment of the invention attached to a surgical drape having a fenestration.

The significance of placing the seam 42 in the back portion 18 can be seen by referring to the attachment of the pouch 10 to the surgical drape 44, such as is shown in FIG. 12. Adhesive or other attachment means 46 (FIGS. 2 and 12) is used to attach, join or mount the pouch to the surgical drape 44. The adhesive 46 can take any manner of forms and configurations, and can be applied in a number of ways. However, the configuration of the adhesive 46 shown in the drawings is suitable for the purposes of the present invention. In the preferred embodiment, the side adhesive portion 46 and the upper edge adhesive portion 52 of the pouch 10 are sprayed-on adhesive that joins the pouch to the surgical drape 44. The upper edge adhesive portion 52 comprises a thin portion preferably extending across the upper edge and a further portion adjacent the top fenestration tape. In this preferred embodiment, the adhesive applied around the fenestration 24 is by double-faced adhesive tape to control the application of adhesive around the fenestration. In another embodiment, all adhesive portions are applied by double-faced adhesive tape.

Preferably, side adhesive strips 46 are applied at an angle 48 relative to the upper back edge 20 for defining the outer portion of the back portion 18 which is attached to the surgical drape 44. Therefore, the portion of the pouch 10 which extends outward away from the side adhesive strips 46 and the drape 44 constitutes the front portion 16, extends away from the back portion 18, and is free to be pulled away from or spaced from the drape and manipulated by the surgical staff. For example, when the drape 44 and pouch assembly 10 is placed over the patient's leg 28, the front portion 16 is pulled away from the back portion 18, and the contour wire 36 is manipulated to form the front portion in the desired configuration. Thereafter, the front portion 16 may be further manipulated or adjusted, or it may simply be accidentally pulled or otherwise stressed. Such movements of the drape may cause undue stress to be applied to the pouch 10, which stress may cause tearing in any unprotected seams. However, in the present invention, the seam 42 is located adjacent the drape 44 and between the side strips 46 so that the attached drape can serve as a reinforcement to the seam 42 and the back portion 18. Thus, any stress which occurs in the front portion 16 is transmitted, if at all, to the combination of the back portion 18 and the drape 44, rather than directly to a seam 42, and such stress would be relieved by movement of the assembly rather than by separation of a seam.

The reinforcement provided by the drape 44 also occurs through joining of the pouch 10 to the drape through other adhesive portions. Fenestration adhesive portions 50 and upper edge adhesive portions 52 may be provided for additional reinforcement. In the preferred embodiment, adhesive areas 46 and the upper edge portion 52 accept sprayed-on adhesive while the fenestration adhesive portions 50 are lined with double-faced adhesive tape with removable liners or release strips 51. The additional adhesive portions 50 and 52 serve to more securely attach the pouch to the drape 44 and minimize the possibility that a stress applied to the front portion 16 is transmitted to the protected seam 42. The seam 42 is protected, in the preferred embodiment, by being bounded by adhesive portions 48–52 on each side of approximately the upper half of the seam 42.

The seam 42, therefore, is preferably positioned approximately in the center of the back portion 18, between the side adhesive strips 46. However, it should be understood that the seam 42 can be positioned elsewhere to still achieve beneficial results provided by the present invention. For example, the seam 42 can be positioned elsewhere on the back portion 18, or on the front portion 16, and still provide benefits in manufacturing and otherwise. Similarly, the pouch 10 may have a number of different seams yet provide the benefits of the present invention by positioning at least one seam 42 between adhesive strips 46 that adjoin the surgical drape 44 and the pouch but there is preferably only one seam, and which is positioned adjacent the drape and between adhesive strips mounting the pouch to the drape.

Figure 2:
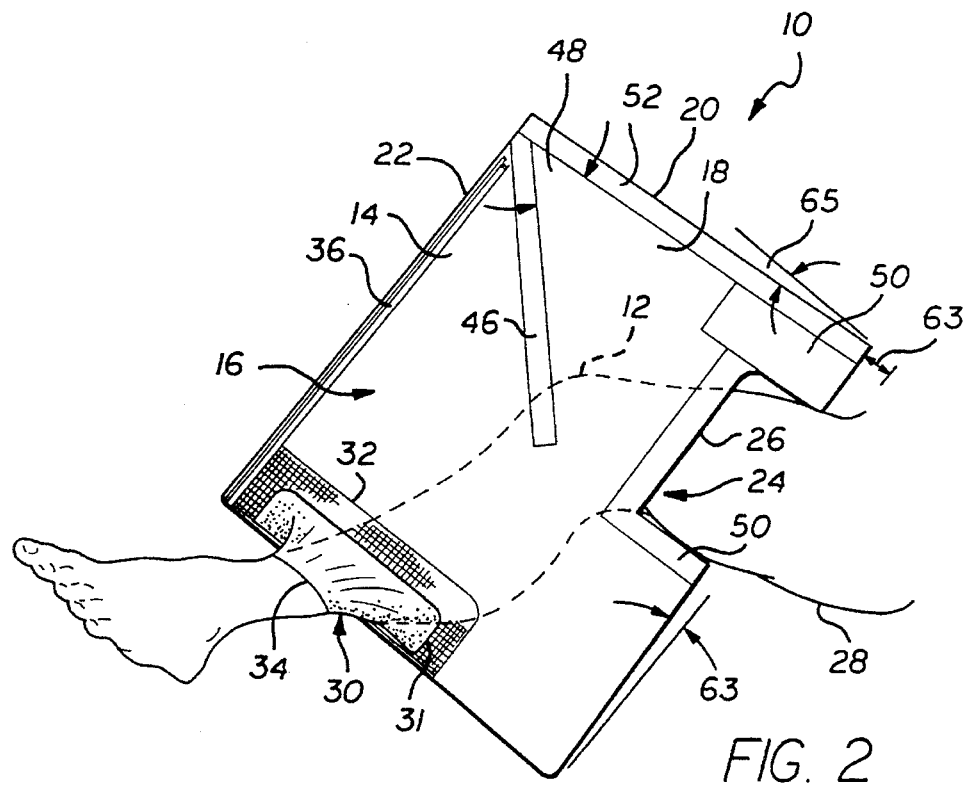
FIG. 2 is a side elevation view of the pouch of FIG. 1 in a partially open position on a patient's leg, omitting the conventional surgical drape, and showing the pouch as it would appear if the left side of the pouch were partially folded toward the right side.

Referring now to FIG. 2, in accordance with one embodiment of the invention, the upper front edge 22 and the upper back edge 20 of the pouch 10 are formed in such a way that a suitably sized concave opening 40 can be formed in the pouch for allowing the surgical team access to the surgical site 12 and to properly channel, collect and contain fluid. In the preferred embodiment, the length of the upper front edge 22 in the sheet 14 is greater than the upper back edge 20 to form the generally concave surface 40 surrounding the surgical site 12. Also in the preferred embodiment, the pouch 10 is formed from a single sheet 14, which may be originally rectangular in shape (FIG. 3). Beginning with a rectangular sheet 14 of appropriate material, cuts may be made (as described more fully below) to form the upper front edge 22, first and second upper back edge portions 54 and 56, respectively, and first and second seam edges 58 and 60, respectively. To provide the desired pouch opening 40 dimensions, the length of the upper front edge 22 is formed longer than the sum of the first and second upper back portions 54 and 56, so that once the complete pouch is formed, the length of the upper front edge 22 is greater than the length of the upper back edge 20.

Figure 13:
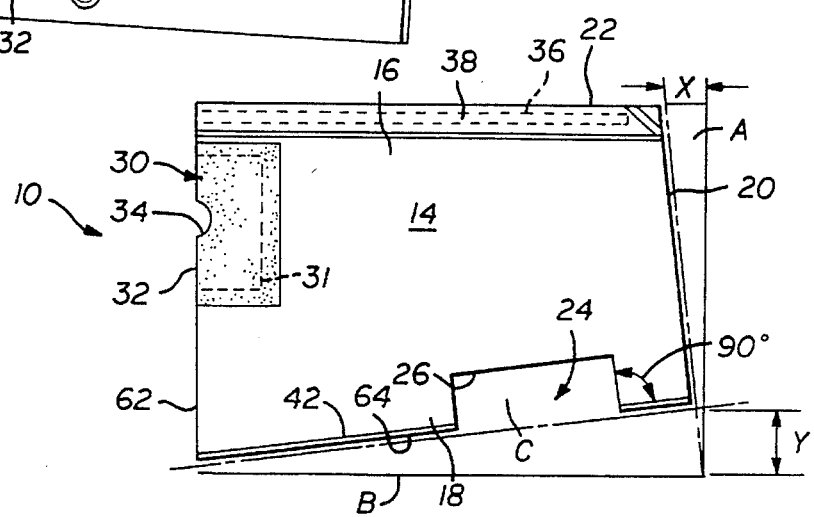
FIG. 13 is a plan view of the preferred embodiment of the invention as shown during a portion of the manufacturing phase in which the flexible sheet of fluid impermeable material is formed so that the front edge of the resulting pouch is not perpendicular to the back edge of the pouch when lying in a flat position.

The opening 40 formed between the upper front 22 and back edges 20 can be made effectively larger, by appropriate cutting of material from the original rectangular sheet of material 14, than otherwise would be available if the sheet were left rectangular when formed into the pouch 10. For example, considering the folded pouch 10 in FIG. 7, folded along fold 62, the angle between the fold 62 and the seam edge 64 is preferably less than 90°, and the angle between the seam edge 64 and the folded upper back edge 20 is also preferably less than 90°. This dimensioning of the material prior to forming the pouch 10 followed by application of the adhesive and then the pouch to the drape 44 reduces the amount or length of material along the upper back edge 20 which is adhered to the drape, and effectively increases the unattached length of the upper front edge 22. The result is a larger opening 40 in the resulting pouch 10. The cut edges are depicted in FIG. 13 as the cut portions A and B. The upper front edge 22 is extended relative to the upper back edge 20 since the front edge is not at a right angle to the upper back edge 20 when portions A and B are removed from sheet 14.

An exit port 66 (FIGS. 1, 3 and 10A–10D) is attached to the sheet 14 which forms the pouch 10. It is desirable to position the exit port 66 in the lower portion of the pouch 10 along or adjacent the center line 78 of the sheet 14, as indicated in FIG. 3, so that fluids may gravitate toward the bottom of the pouch 10 and be removed through the exit port 66. In one embodiment of the invention, a hole 68 is formed in the sheet 14 to accommodate the exit port 66. As shown in FIG. 10A, the exit port 66A may have a removable plug 70 that it is replaceable over the exit port 66A opening to contain fluid in the pouch 10. In another embodiment, the port 66B has an opening to be cut open as shown in FIG. 10B and attached to a tube to remove fluids from the pouch 10. The port 66A–B includes a crown 72 and washer 74 to retain the port in a fixed position and sealed with respect to the pouch 10 by a friction fit. In another embodiment, as shown in FIG. 10C, a fluid-tight seal is created between a one piece exit port 66C and the pouch 10 by heat sealing the bottom portion 76 of the port 66C onto the immediate sheet area surrounding the hole 68 in sheet 14. In a further preferred embodiment, as shown in FIG. 10D, the bottom portion of the port 66D is formed with ridges to permit the flow of fluid through the port even when the pouch is lying flat.

The present invention also provides an economical method of manufacturing a fluid collection pouch formed from one sheet of material having edges that may be joined together with a single seal to form a pouch. In the preferred embodiment of the invention, a flat sheet of preferably fluid impermeable material 14 is selected to form the pouch 10. The top edge of the sheet 14 is folded over to form a channel 38 and the upper front edge 22 of the pouch 10. A portion of the channel 38 material is thermally or adhesively sealed along the front edge 22 to form a continuous tube or closed channel 38.

After the channel 38 is formed, an opening or fenestration 30 is cut at walls 31 from the central portion sheet of material 14 preferably symmetrically about a center line 78 as in FIG. 3. The size of this fenestration 30 is sufficient shown to receive a portion of a patient's body, such as a leg 28. A sheet of elastomeric material 32 covers and overlaps the opening 30 in the sheet 14 as shown in FIGS. 4–5. It is preferable to join the elastomeric covering 32 over the opening 30 by heat sealing, by ultrasonic sealing techniques, or that it be capable of forming a seam through the use of an adhesive. The elastomeric sheet 32 may be made of a variety of materials such as Kraton which is supplied by the Clopay company.

During the manufacture of the pouch 10, as illustrated in FIGS. 7 and 13, the sheet 14 of fluid impermeable material is next folded in half along the center line 78 of the sheet (FIG. 3). In the preferred embodiment, a triangular portion A of the folded sheet 14 of fluid impermeable material is removed from the sheet. A segment of portion A, which is along the same edge as the upper front edge 22 as illustrated in FIG. 13,, is identified as segment X. It is preferable for segment X to be such a length so that the upper front edge 22 of the folded sheet 14 has a length of about 24 inches.

Another triangular portion B of the folded sheet 14 is removed as shown in FIG. 13. A segment of portion B, which is along the same edge as the upper back edge 20 as illustrated in FIG. 13, is identified as segment Y. It is also preferable for segment Y of portion B to be such a length so that the upper back edge 20 is about 19 inches when folded flat in a side-to-side position. During this phase of manufacture, waste is greatly minimized since only portions A and B are discarded as scrap material. Although the lengths of segments X and Y may vary according to patient size and available stock material, the preferred dimensions of the remaining portions of the folded sheet after cutting ensure an extended pouch opening or surface 40 for greater exposure to the surgical site 12.

After both portions A and B have been removed from the folded sheet 14, a seam 42 is formed along an edge 64 of the sheet that was adjacent to removed portion B. The seam 42 is preferably formed by a thermoimpulse pressure bar, or may be formed by other heat sealing or ultrasonic techniques. As shown in FIG. 7, the pouch 10 is folded along fold 62 so that the angle 63 between the fold 62 and the seam edge 64 is preferably less than 90°, and the angle 65 between the seam edge 64 and the folded upper back edge 20 is preferably less than 90°.

Referring now to FIGS. 7 and 12–13, the preferred embodiment of the invention has an opening or fenestration 24 on the back portion 18 of the pouch 10 that accepts the part of the body that is being operated on such as the leg of a patient 28. The fenestration 24 preferably is located below the upper back edge 20 and centrally along the seam 42. This opening 24 is formed by removing an additional portion of the folded sheet 14 along the seal edge 64. This portion is identified as portion C as illustrated in FIG. 13. The removed portion C defines the walls 26 of the fenestration 24. In the preferred embodiment, the respective formed walls 26 of the fenestration 24 are parallel to the upper back edge 20 of the folded sheet 14, and parallel to the seal edge 64.

Referring now to FIG. 13 again, in the preferred embodiment of the invention, the draw wire 36 is inserted into the channel 38 along the upper front edge 22 of the folded sheet 14. The ends of channel 38 are then closed, preferably by heat sealing, thereby containing the draw wire 36 within the channel 38. In general, the draw wire 36 may be formed from a malleable and conformable material. For instance, the draw wire 36 may be formed from two wires surrounded by a relatively soft flexible protective layer 37 as shown in FIGS. 9A and 9B. The purpose of the protective layer 37 is to prevent the wire from puncturing the sheet 14 of the pouch 10.

In another embodiment of the invention as illustrated in FIGS. 1–4 and 9A, a portion of the draw wire 36 may be directly attached to the upper front edge 22 of the pouch 10. The draw wire 36 may be secured to the pouch 10 by applying adhesive over the surface area of the wire protective layer 37 that is joined with the sheet 14. As a result, when front edge 22 is pulled forward and away from the back edge 20 and the back portion 18, the front edge 22 will form a generally concave surface 40 to expose the surgical site 12.

Figure 11:
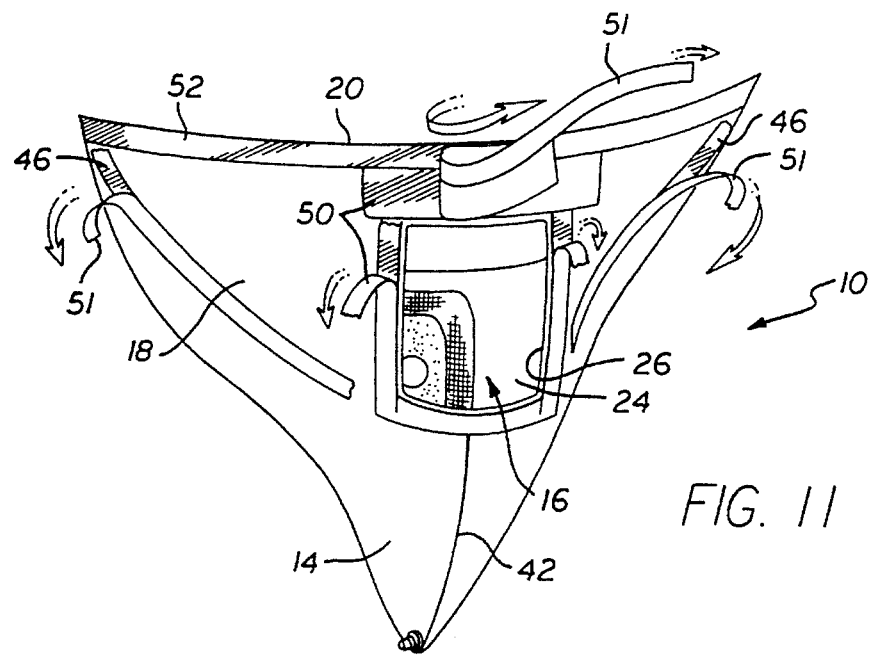
FIG. 11 is a rear perspective view of one embodiment of the present invention showing adhesive strips, covered by release paper, for use in attaching the pouch to a conventional drape.

Referring now to FIGS. 3, 7 and 11–12, various adhesive surfaces are applied to the back portion 18 of the pouch 10. The pouch 10 in the preferred embodiment of the invention has adhesive strips 50 formed around the fenestration 24 located on the back portion 18 of the pouch 10. Other adhesive strips 46 and 52 may be placed at various locations on the back portion 18 of the pouch 10 for joining with a surgical drape 44. In one embodiment, adhesive strips 46 and 52 are sprayed-on adhesive. A layer of sprayed-on adhesive may also be applied in the area between the upper edge adhesive portion 52 and the top fenestration adhesive portion 50. These adhesive portions 46, 50 and 52 may also be formed by pieces of double-faced adhesive tape with removable linings or release strips 51 that are peeled back and removed before use as depicted in FIGS. 8 and 11. After the removable strips 51 are peeled back, the pouch 10 may be attached to a surgical drape 44 through the exposed adhesive surfaces of the double-faced tape 46, 50 and 52 located on the back portion 18 of the pouch 10.

The side adhesive portions preferably extend along a line (not shown) running approximately from the corner, between the upper front and back edges toward the port 66. As seen in FIG. 7, the side adhesive portions 46 are not exactly aligned but approximately. Additionally, the adhesive portions 50 and 52 that are above the back fenestration 24 combined are wider than the rest of the adhesive portions 50 around the back fenestration to provide greater support for the pouch and the seam 42. The fenestration adhesive portions 50 are preferable one inch wide. In the preferred embodiment, it is preferable not to spray on adhesive portions 50 that surround the back fenestration 24 since this may introduce adhesive spray into the relatively sterile interior environment of the pouch through the back fenestration.

In the preferred embodiment, as shown in FIG. 12, a surgical drape 44 is attached to the back portion 18 of the pouch 10. The surgical drape 44 preferably has a fenestration 45 to receive a member of the patient's body that is being operated on such as a leg 28. It is preferable for the fenestration 45 in the surgical drape 44 to be located over the back portion fenestration 24 of the pouch 10 so that the body part being operated on may pass through the drape fenestration 45, the fenestration 24 in the back portion of the pouch, and finally out through the elastomeric fenestration 34 in the front portion 16 of the pouch 10.

In the preferred embodiment, the surgical drape 44 is also attached to the pouch 10 by sprayed-on adhesive 46. The sprayed-on adhesive area 52 preferably runs along the backside of the upper back edge of the pouch 10, and along the area between the back fenestration 24 and the upper back edge. In addition, it is preferable to use a sprayed-on adhesive 46 to join the pouch 10 and the drape 44 along the backside of the pouch along a line from the upper back edge corners of the pouch down toward the exit port 66 as shown in FIG. 12. However, it is still preferable for the fenestration adhesive strips 50 to be formed from double-faced adhesive tape with release tape 51. It is preferable for the seam 42 to be located in between at least two adhesive surfaces 46 on the back portion 18 of the pouch 10 as illustrated in FIG. 12. When pulling the upper front edge 22 of the pouch 10 to expose the surgical site 12, any tearing stress or force applied to the pouch is first absorbed by the pouch and drape along the adhesive surfaces 46 of the pouch 10 that joins the surgical drape 44. As a result, protection of the seam 42 of the pouch 10, positioned in between adhesive portions 46, reduces the risk of fluid leakage from the pouch.

The immediate area of the fluid pouch 10 surrounding the back portion fenestration 24 is preferably covered with double-faced adhesive tape 50 and release strips 51. It is preferable for the adhesive surfaces of the double-faced tape 50 to be covered with four separate liners, including a top and a bottom portion as well as two side portions, to surround the back fenestration 24 of the fluid collection pouch 10.

In general, the pouch 10 may be formed from a variety of materials. In the preferred embodiment, however, the pouch 10 is formed from a transparent flexible material which does not allow liquid to pass therethrough. Examples of such fluid impermeable materials include a variety of polymeric films such as polyethylene, polypropylene, polyester, polyvinylchloride, or a combination thereof. Another desirable feature of the material chosen to form the pouch 10 is that it be sealable to itself through the use of a thermoimpulse pressure bar, other heat or ultrasonic sealing techniques, or that it be capable of forming a seam through the use of an adhesive. In another embodiment of the invention, thicker material is not required to form the pouch since the risk of leakage or tearing is reduced by using only one folded sheet of material 14 that does not have a tendency to come apart such as the prior pouches formed from multiple sheets.

The pouch 10 also may be formed from an opaque material or may include gradations on a portion of the pouch to measure the amount of fluid that is captured in the pouch.

The actual thickness of the sheet of flexible fluid impermeable material 14 may also vary. Although previous fluid collection pouches have been constructed so as to require sheet material up to 7 millimeters in thickness, the preferred thickness of the sheet in the present invention is approximately 4–5 millimeters. In one embodiment of the invention, a thinner sheet material 14 may be used since the pouch 10 is formed with a single seam or seal 42 that is positioned in a manner resistant to tearing.

Although the present invention has been described in detail with reference only to the presently preferred embodiments, it will be appreciated by those of ordinary skill in the art that various modifications can be made without departing from the spirit of the invention. Accordingly, the invention is limited only by the following claims.

What is claimed is:

1. An arthroscopic pouch for use with a surgical drape, the pouch comprising:

a single folded sheet of flexible fluid impermeable material having a front portion with a central region and an upper front edge having a length furthest away from a patient when disposed on a patient, the central region of said front portion having a first fenestration for receiving a leg, a back portion with a central portion and an upper back edge having a length nearest the patient when disposed on a patient, the central region of said back portion having a second fenestration for receiving the leg, and only a single seam formed on said back portion by joining edges of said folded sheet to form the pouch wherein the single folded sheet formed with the single seam in a folded shape has a fold and at least a first outer perimeter side defined by the seam, a second outer perimeter side defined by the fold, a third outer perimeter side substantially opposite the first side and a fourth outer perimeter side substantially opposite the second side, wherein the first and second sides join to form an angle less than 90° and the first and fourth sides join to form an angle less than 90° and wherein the fourth side defines the upper back edge, and a layer of adhesive applied to the back portion of said folded sheet adjacent the upper back edge wherein the length of the upper back edge of said back portion is defined by said layer of adhesive such that the length of the upper front edge is greater in length than the length of the fourth outer perimeter side and greater than the length of the upper back edge.

a layer of adhesive applied to the back portion of said folded sheet adjacent the upper back edge wherein the length of the upper back edge of said back portion is defined by said layer of adhesive Such that the length of the upper front edge is greater in length than the length of the fourth outer perimeter side and greater than the length of the upper back edge.

2. An arthroscopic pouch as recited in claim 1 wherein said sheet of flexible fluid impermeable material is a polyethylene film.

3. An arthroscopic pouch as recited in claim 1 wherein said single seam joining said folded sheet is formed by heat sealing.

4. An arthroscopic pouch as recited in claim 1 wherein said sheet of flexible fluid impermeable material is lined with double-faced adhesive strips of tape surrounding the second fenestration in said back portion of said flexible sheet.

5. An arthroscopic pouch as recited in claim 4 wherein said adhesive strips are covered with removable backings that are removed prior to use.

6. An arthroscopic pouch as recited in claim 1 wherein said sheet of flexible fluid impermeable material is attached to a surgical drape having a fenestration corresponding to said second fenestration of said back portion of said pouch.

7. An arthroscopic pouch as recited in claim 6 wherein said surgical drape is attached to said sheet of flexible fluid impermeable material by a sprayed-on adhesive located on the surfaces of said sheet that contact said surgical drape.

8. An arthroscopic pouch as recited in claim 7 wherein said single seam is located in between adhesive portions of said back portion of said pouch, said location of adhesive portions thereby reinforcing said back portion to protect said seam.

9. An arthroscopic pouch as recited in claim 1 wherein a fenestration covering for said first fenestration is heat sealed to the peripheral edges of said pouch surrounding said first fenestration of said front portion.

10. An arthroscopic pouch as recited in claim 1 wherein said membrane covering for said first fenestration is Kraton.

11. An arthroscopic pouch as recited in claim 1 wherein said upper front edge of said pouch is held in an open position to control fluids at a surgical site by a contoured wire maintaining said upper front edge of said pouch in an outward position.

12. An arthroscopic pouch as recited in claim 11 wherein said contoured wire is a plastic coated metal wire.

13. An arthroscopic pouch as recited in claim 1 further including a port, wherein said port is heat sealed onto a portion of said pouch.

14. An arthroscopic pouch as recited in claim 13 wherein said port is formed with a one-piece construction.

15. An arthroscopic pouch for use with a surgical drape, the pouch comprising:

a single folded sheet of flexible fluid impermeable material having a fold and having first and second edges joined in a seam, at least two spaced apart adhesive portions applied to the sheet for attachment to the surgical drape, and a front portion furthest away from a patient and a back portion nearest the patient, said front portion having a front fenestration for receiving an appendage of the patient, said back portion having a back fenestration for receiving the appendage of the patient wherein the back fenestration for receiving an appendage is substantially surrounded by said first adhesive portion and said second adhesive portion is applied spaced apart from said first adhesive portion on said sheet, and wherein the seam joining the edges of said folded sheet to form the pouch is positioned within the second adhesive portion and wherein the single folded sheet formed with the single seam in a folded shape has at least a first outer perimeter side defined by the seam, a second outer perimeter side defined by the fold, a third outer perimeter side substantially opposite the first side and a fourth outer perimeter side substantially opposite the second side, wherein the first and second sides join to form an angle less than 90° and the first and fourth sides join to form an angle less than 90° and wherein the fourth side defines the upper back edge.

16. An arthroscopic pouch as recited in claim 15 further comprising a drape, wherein the at least two spaced apart adhesive portions joins the pouch to the drape and wherein the seam is adjacent the drape.

17. An arthroscopic pouch as recited in claim 15 wherein the pouch further includes an adhesive portion extending transversely of the seam for joining a portion of the pouch to the drape.

18. An arthroscopic pouch as recited in claim 15 wherein the back fenestration includes walls defining the fenestration and wherein the walls include adhesive portions for joining the walls to the drape.

19. A method of manufacturing an arthroscopic pouch for use with a surgical drape comprising the steps of:

selecting a single flexible sheet of fluid impermeable material with a top edge, a bottom edge and two opposite edges with respect to a center line of said sheet, folding said top edge creating a channel defined by the sheet and the folded portion of said top edge for receiving a draw wire, joining said folded portion of said top edge to said sheet enclosing a portion of said channel, forming a first fenestration along said center line for receiving a limb, applying a fenestration covering over said first fenestration, folding said sheet along said center line, removing a portion of said folded sheet along at least one of said overlapping bottom edge, top edge, and two opposite edges, joining the overlapping bottom edges of said sheet to form the only seam in said fluid collection pouch, forming a second fenestration along said bottom edge for receiving a limb, inserting a draw wire into said channel along the length of said top edge, and applying adhesive along both sides of said only seam of said pouch for attachment to the surgical drape.

20. A method of manufacturing an arthroscopic pouch to be used for collecting fluids at a surgical site, the method comprising the steps of:

selecting a sheet of flexible fluid impermeable material with a top portion and top edge, a bottom portion and a bottom edge and first and second substantially opposite side portions and side edges, folding said sheet substantially along an approximate center line of said sheet forming a fold having a given length and bringing said side edges together in overlapping position, removing at least a first angled portion from one of said top, bottom and side portions of said sheet, said first removed angled portion of said sheet consisting of an area along a separated edge leaving one of said other edges adjacent the separated edge shorter in length than the separated edge while leaving the fold length substantially unchanged, and sealing one of said folded top and bottom edges of said folded sheet to form a fluid collection pouch.

21. The method as recited in claim 20 wherein said sheet is folded along said center line to form a polygon having at least four sides.

22. The method as recited in claim 21 wherein the step of removing a first angled portion includes the step of removing an angled portion from the bottom portion, and further comprising the step of removing a second angled portion from the side portion.

23. The method as recited in claim 22 wherein the step of removing first and second angled portions includes the steps of removing the first angled portion larger than the second angled portion such that four edges of the folded sheet are of different lengths.

24. The method as recited in claim 20 further comprising the step of applying adhesive to an area of said pouch on both sides of said seam for attachment to the surgical drape.

25. The method as recited in claim 20 further comprising the step of forming an opening in at least one of the edge portions for forming a fenestration.

26. The method as recited in claim 25 wherein the step of forming an opening includes the step of forming an opening in the bottom side portion, wherein the folded sheet includes a folded side and further comprising the step of forming a second opening in the folded side for forming a fenestration, and wherein the step of sealing includes the step of sealing the edge of the bottom portion.

27. The method as recited in claim 20 further comprising the step of applying an adhesive layer along an edge defined by the edge of the opposite side portions for attaching the pouch to a drape.

* * * * *